United States Patent [19]

Heller et al.

[11] Patent Number: 5,071,416

[45] Date of Patent: Dec. 10, 1991

[54] METHOD OF AND APPARATUS FOR LASER-ASSISTED THERAPY

[75] Inventors: Donald F. Heller, Warren; John C. Walling, White House Station, both of N.J.; Robert S. Anderson, Livermore, Calif.

[73] Assignee: Metalaser Technologies, Inc., Pleasanton, Calif.

[21] Appl. No.: 517,762

[22] Filed: May 2, 1990

[51] Int. Cl.⁵ .............................................. A61B 6/00
[52] U.S. Cl. ...................................... 606/3; 606/10; 128/395; 128/665
[58] Field of Search ............. 606/2, 3, 10–18; 604/20, 21, 49; 128/633, 395–398, 665; 372/3; 310/426, 427

[56] References Cited

U.S. PATENT DOCUMENTS

| | | | |
|---|---|---|---|
| 4,336,809 | 6/1982 | Clark | 128/665 |
| 4,648,714 | 3/1987 | Benner | 356/301 |
| 4,676,639 | 6/1987 | Van Wagenen | 356/246 |
| 4,784,450 | 11/1988 | Jain et al. | 350/96.15 |
| 4,791,927 | 12/1988 | Menger | 606/3 |
| 4,832,483 | 5/1989 | Verma | 356/39 |
| 4,932,934 | 6/1990 | Dougherty et al. | 604/21 |
| 4,957,481 | 9/1990 | Gatenby | 604/20 |

FOREIGN PATENT DOCUMENTS 8702884  5/1987  Fed. Rep. of Germany.

Primary Examiner—Stephen C. Pellegrino
Assistant Examiner—Steven J. Shumaker
Attorney, Agent, or Firm—Heller, Ehrman, White, McAuliffe

[57] ABSTRACT

A laser beam from a tunable solid state laser such as an alexandrite laser passes through a Raman shifter to produce a Raman-emitted beam with wavelength shifted so as to be able to activate a preselected photosensitizer for medical treatment. A combination of a laser and a Raman shifter with or without additionally a harmonic generator such as a frequency doubler may be also selected such that radiation with two different wavelengths can be obtained for treatment and detection.

27 Claims, 2 Drawing Sheets

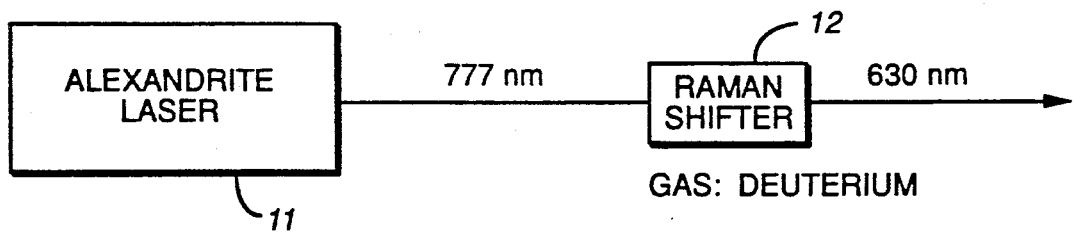
FIG._1A
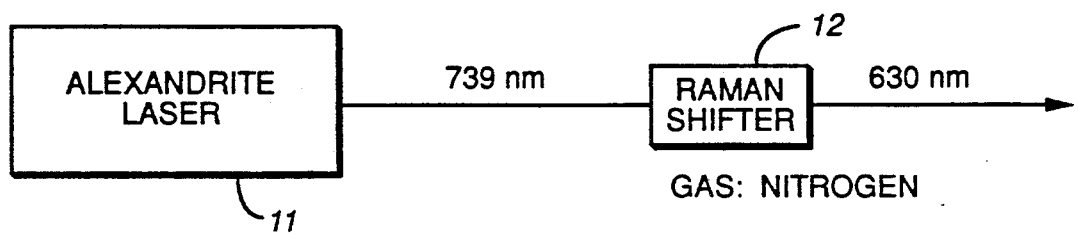
FIG._1B
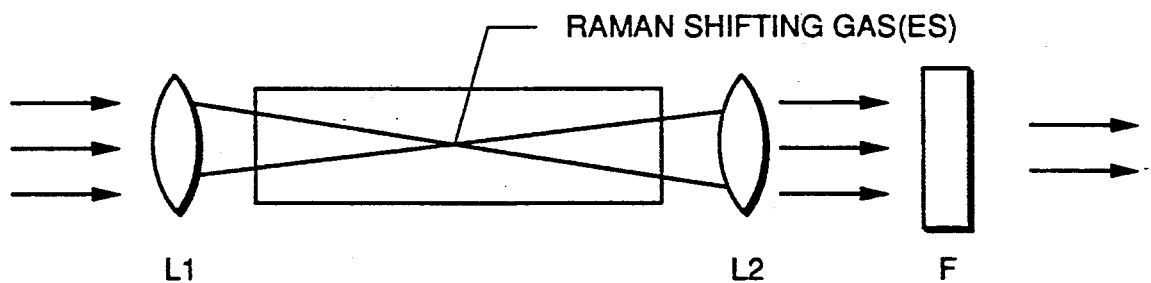
FIG._1C
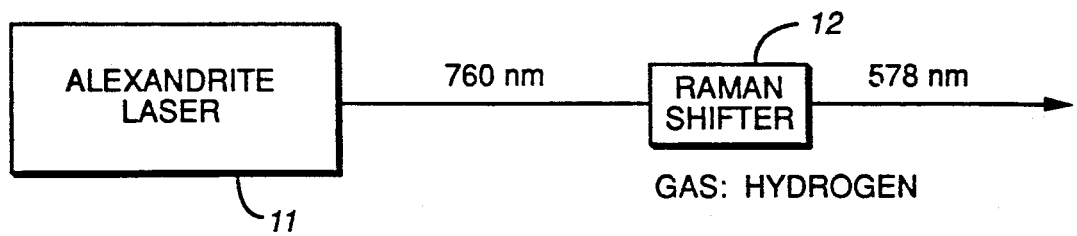
FIG._2

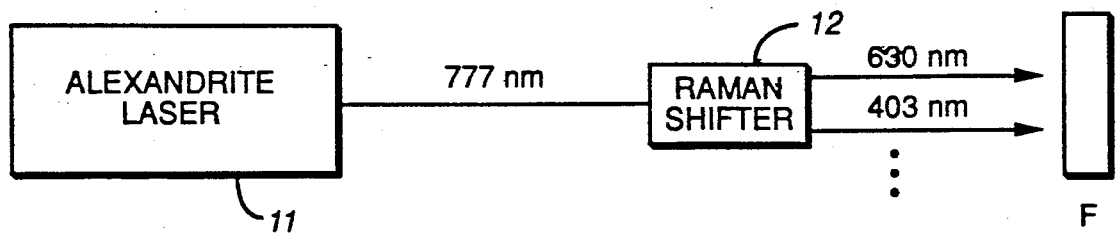
FIG._3A
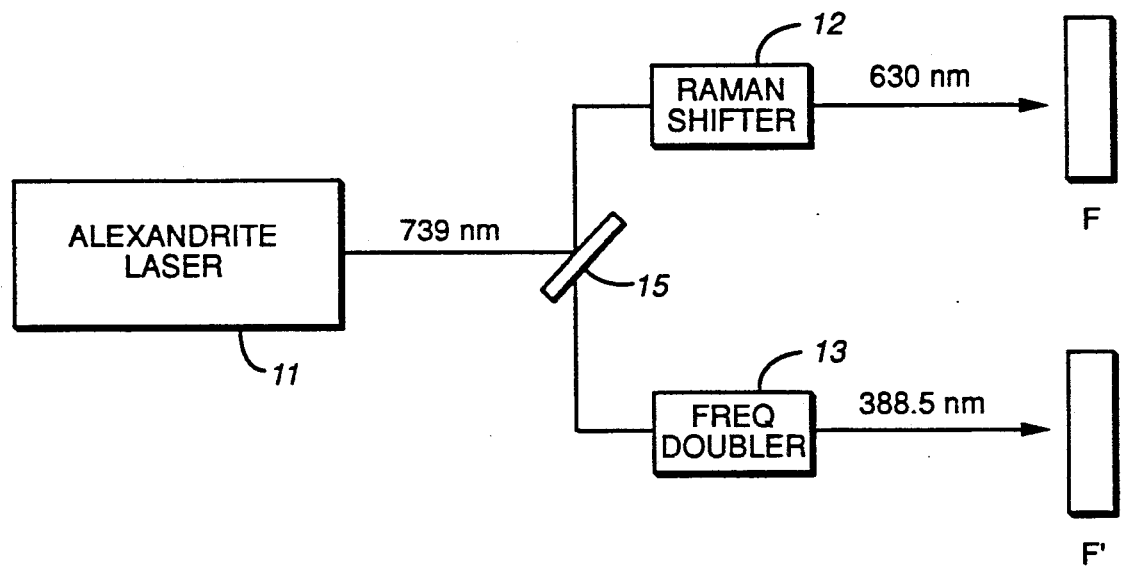
FIG._3B
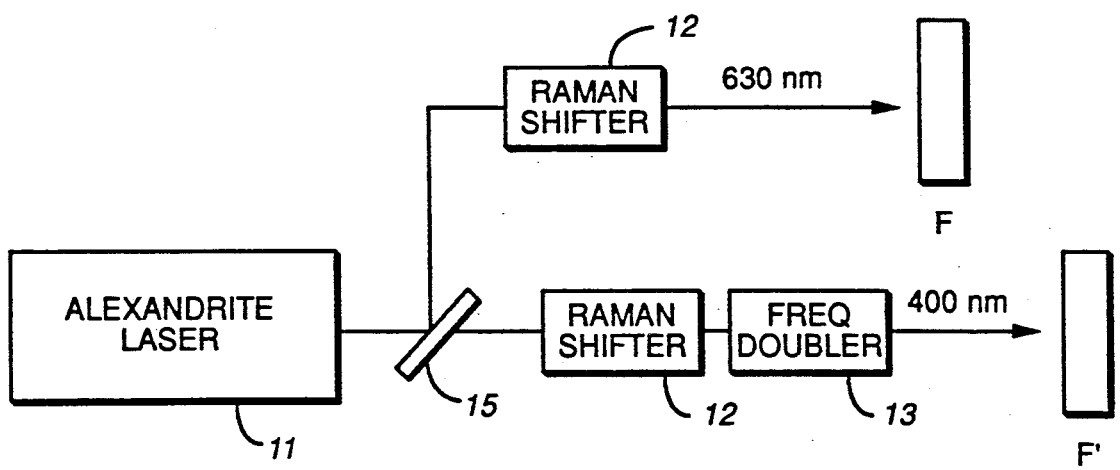
FIG._3C

METHOD OF AND APPARATUS FOR LASER-ASSISTED THERAPY

BACKGROUND OF THE INVENTION

This invention relates to methods of and apparatus for laser-assisted therapy including photodynamic therapy.

Photodynamic therapy (PDT) with laser is being regarded as an effective method for treatment of cancer and other disorders. As with antibiotherapy, tumor cultures are initiated in laboratories and tested for sensitivity to various sensitizing agents and various laser wavelengths before the method is applied clinically. Currently known examples of sensitizing compound include dihematoporphyrin-ether activated at wavelength of 630 nm, benzo-porphyrin derivative activated at wavelength of 690 nm and tin [4]etiopurpurin dichloride (SnET2 purpurin) activated at wavelength of 660–670 nm. Many other sensitizing agents and new laser wavelengths are likely to be developed. At the present time, argon-pumped dye lasers, copper-pumped dye lasers, gold lasers, excimer-pumped dye lasers or the like are used but lasers of these types are not reliable, versatile or convenient in providing a laser beam of desired power and wavelength for the aforementioned medical applications.

SUMMARY OF THE INVENTION

It is therefore an object of the present invention in view of the above to provide methods of and apparatus for laser-assisted photodynamic and other types of therapy.

It is another object of the present invention to provide such methods and apparatus which are efficient and convenient.

The methods and apparatus with which the above and other objects can be achieved are based on stimulated Raman emission, sometimes called stimulated Raman scattering. Stimulated Raman scattering is a means for "pumping" light, or converting light at a certain wavelength into light at longer ("Stokes") or shorter ("anti-Stokes") wavelengths. If the pump light is sufficiently intense, the stimulated Raman scattering process can be highly efficient. Energy conversion efficiencies into Stokes and anti-Stokes wavelengths in excess of 70% have been reported. According to the present invention, a combination consisting of a laser and a Raman shifter is selected such that the beam of radiation having a certain wavelength which can be caused to be emitted from the laser, when traversed through the Raman shifter, produces frequency-shifted scattered laser light (or Raman-emitted) having a desired wavelength. If the method or apparatus is for photodynamic therapy with the use of dihematoporphyrin-ether, the desired wavelength is approximately 630 nm. If benzo-porphyrin derivative is the sensitizing agent to be used, the desired wavelength will be approximately 690 nm. If SnET2 purpurin is to be used, the desired wavelength will be approximately 660 nm. For treatment of vascular lesions, a laser beam with a much shorter wavelength (say, 578 nm) may be desirable. A tunable solid state laser such as an alexandrite laser or a titanium sapphire laser is preferably used in such a combination. Since many different Raman shifters with different scattering media, and hence different shift characteristics, are available, different combinations of a laser and a Raman shifter are capable of outputting laser radiation with a desired wavelength but a selection is made according to the present invention such that the scattered frequency-shifted Raman-emitted beam with the desired wavelength is outputted in an optimum condition for the intended use.

Such a frequency-shifted Raman-emitted laser light can be used not only for the purpose of photodynamic or other kind of therapy but also for detection, for example, of a malignant condition. For such a purpose, a laser beam with lower intensity and different wavelength may be used to cause fluorescence of an injected tumor-seeking agent. Thus, a Raman shifter capable of producing Raman-emitted light having two different wavelengths may be selected such that the same combination of a laser and a Raman shifter can be used both for treatment at one wavelength and for detection and localization of a condition at another wavelength.

As an alternative, a harmonic generator such as a frequency doubler may be selectably used in combination with the laser to produce a beam of radiation suited for such detection separate from the beam which is intended for treatment.

It has not been known or appreciated that pulsed laser sources having sufficient intensity to produce efficient stimulated Raman scattering are compatible with the requirements for efficacious photodynamic therapy, and thus can prove useful as sources for photodynamic therapy.

BRIEF DESCRIPTION OF THE DRAWING

The accompanying drawings, which are incorporated in and form a part of the specification, illustrate embodiments of the present invention and, together with the description, serve to explain the principles of the invention. In the drawings:

FIGS. 1A and 1B are block diagrams schematically showing the structure and operation of apparatus embodying the present invention for laser-assisted photodynamic therapy using dihematoporphyrin-ether and FIG. 1C is a schematic drawing for showing the structure of the Raman shifter in FIGS. 1A and 1B, FIG. 2 is a block diagram schematically showing the structure and operation of another apparatus embodying the present invention, and FIGS. 3A, 3B and 3C are block diagrams schematically showing the structures and operations of still other apparatus embodying the present invention.

In these figures, components which are substantially identical or at least similar to each other are indicated by the same numeral.

DETAILED DESCRIPTION OF THE INVENTION

With reference to FIGS. 1A and 1B which schematically show systems for laser-assisted photodynamic therapy using dihematoporphyrin-ether, numeral 11 indicates a source of a laser beam including an alexandrite laser such as a PAL TM system (produced and sold by Light Age, Inc. of Warren, N.J.) which is a tunable solid state laser with output wavelength in the range of about 720–800 nm. Numeral 12 generally indicates a Raman shifter with means (not shown) for applying Raman-shifted radiation on a target region, having a typical optical arrangement shown schematically in FIG. 1C and only for the purpose of illustration. Monochromatic radiation from the laser 11 impinges on an emitting medium in an appropriate transparent cell.

The impinging laser light may be condensed by a lens $L_1$ and collimated by another lens $L_2$, and unwanted radiation from the beam may be removed by a narrow-band optical filter F.

Use as the Raman shifter 12 may be made, for example, of Model LAI101 PAL-RC (produced and sold by Light Age, Inc.) with hydrogen, deuterium, methane, nitrogen, oxygen or other gases used as the Raman emitting medium. Table 1 shows the wavelengths of Raman-shifted beams (first, second, etc.) emitted from such shifters using different kinds of gas when laser beams of different initial wavelengths impinge thereupon. Liquid and solid media may also be employed but their use is generally less preferable. If deuterium gas is employed in the Raman shifter 12 in combination with monochromatic pump radiation of wavelength near 777 nm as shown in FIG. 1A, anti-Stokes light is generated at a wavelength near 630 nm. Pump beams having low spatial divergence and powers of several megawatts are preferred.

The foregoing description of a preferred embodiment of the invention has been presented for purposes of illustration and description. It is not intended to be exhaustive or to limit the invention to the precise form disclosed, and many modifications and variations are possible in light of the above teaching. For example, the source of laser radiation need not be an alexandrite laser. A titanium sapphire laser and other kinds of tunable solid state laser may be used as the source of laser radiation. Other examples of sensitizing agent to be activated by a laser beam in photodynamic therapy according to the present invention include but are not limited to benzo-porphyrin derivative and SnET2 purpurin although only such agents that can be activated by radiation in the wavelength range of 630 nm–690 nm are considered herein. Raman-emitted radiation outside this wavelength range may be utilized for different medical purposes and the method and apparatus therefor, such as shown in FIG. 2, are also to be considered within the scope of this invention. Some additional combinations of initial laser wavelength and the kind of gas used in a Raman shifter which may produce useful Raman-emitted radiation within the broad meaning of the present invention are also included in Table I.

Another method embodying the present invention is based on the observation that the Raman spectrum of many scattering (emitting) substances contains a plurality of anti-Stokes lines. In such a case, a high-intensity line may be used for treatment and a low-intensity line corresponding to a different wavelength may be used for detection and/or localization, say, of a malignancy by causing a photosensitizer to fluoresce. For example, under typical conditions of intensity, pressure and focussing geometry where pump light at 777 nm, as can be generated by using an alexandrite laser, is anti-Stokes Raman-shifted to produce light at 630 nm as described above, light is also produced at higher-order anti-Stokes wavelengths of 530 nm, 457 nm, 402 nm, etc. as shown in FIG. 3A and Table 1. Although the light intensity at these wavelengths is significantly lower than at 630 nm, there is more than enough intensity generated for use for tumor detection and localization. With dihematoporphyrin-ether, light with wavelengths in the 450-350 nm region is particularly well suited to this application as it is strongly absorbed, is well transmitted by optical fibers, and is non-mutagenic. In FIG. 3A, F indicates a filter which may be used for selectively allowing Raman-emitted radiation in a specified wavelength range.

According to still another method embodying the present invention and schematically illustrated in FIG. 3B, the laser radiation from the laser 11 is passed selectably through a Raman shifter 12 and a harmonic generator such as a frequency doubler 13 wherein numeral 15 indicates a device of any known type for selectably directing the laser beam emitted from the laser 11 to the Raman shifter 12 or the frequency doubler 13. The Raman shifter 12 can serve to activate a photosensitizer for treatment as described above. The frequency doubler 15 serves to provide a beam with a higher frequency (shorter wavelength) that may be used for the purpose of detection and/or localization as above.

The methods described above by way of FIGS. 3A and 3B can be combined to form another combination as illustrated in FIG. 3C which is characterized as having another Raman shifter 12' inserted between the frequency doubler 13 and the beam-splitting means 15. Table 2 shows examples of combination of wavelengths that may thus be obtained from an initial laser beam and a combination of a Raman shifter and a frequency doubler. In FIGS. 3B and 3C, F and F' indicate individual optical filters which can be operated such that laser light of a different wavelength cab be selectably caused to be outputted.

In all examples described above, furthermore, it is believed preferable to use a Q-switched laser but use may well be made of a mode-locked laser. Lasers of other types are not intended to be precluded. In all block diagrams presented above, the boxes representing a laser and those representing a Raman shifter were drawn separately but this is not intended to preclude the designs whereby the Raman shifter 12 is located inside the resonator cavity of the laser 11. In summary, any such modifications and variations that may be apparent to a person skilled in the art are intended to be included within the scope of this invention.

TABLE 1

| Gas | Fundamental | 1st Shift | 2nd Shift | 3rd Shift | 4th Shift |
|---|---|---|---|---|---|
| Oxygen | 720 nm | 647 nm | 588 nm | 539 nm | 497 nm |
| Oxygen | 740 | 664 | 601 | 550 | 507 |
| Oxygen | 760 | 680 | 615 | 561 | 516 |
| Oxygen | 780 | 696 | 628 | 572 | 525 |
| Oxygen | 800 | 711 | 641 | 582 | 534 |
| Deuterium | 720 | 592 | 503 | 437 | 387 |
| Deuterium | 740 | 606 | 513 | 445 | 393 |
| Deuterium | 760 | 619 | 522 | 452 | 398 |
| Deuterium | 780 | 632 | 532 | 459 | 403 |
| Deuterium | 800 | 646 | 541 | 466 | 409 |
| Nitrogen | 720 | 617 | 539 | 479 | 431 |
| Nitrogen | 740 | 631 | 550 | 488 | 438 |
| Nitrogen | 760 | 646 | 561 | 496 | 445 |
| Nitrogen | 780 | 660 | 572 | 505 | 452 |
| Nitrogen | 800 | 674 | 583 | 513 | 458 |
| Hydrogen | 720 | 554 | 450 | 379 | 328 |
| Hydrogen | 740 | 566 | 458 | 385 | 332 |
| Hydrogen | 760 | 578 | 466 | 390 | 336 |
| Hydrogen | 780 | 589 | 473 | 395 | 340 |
| Hydrogen | 800 | 600 | 481 | 401 | 343 |
| Hydrogen | 760 | 578 | 466 | 390 | 336 |
| Deuterium | 777 | 630 | 530 | 458 | 403 |
| Oxygen | 735 | 660 | 598 | 547 | 504 |
| Oxygen | 773 | 690 | 623 | 568 | 522 |
| Nitrogen | 739 | 630 | 550 | 487 | 438 |
| Nitrogen | 780 | 660 | 572 | 505 | 452 |

TABLE 2

|  | Fundamental | 1st Shift | Doubled | Doubled |
|---|---|---|---|---|
| Hydrogen | 735 nm | 1058 nm | 529 nm | 368 nm |
| Hydrogen | 780 | 1154 | 577 | 390 |

TABLE 2-continued

| | Fundamental | 1st Shift | Doubled | Doubled |
|---|---|---|---|---|
| Deuterium | 735 | 942 | 471 | 368 |
| Deuterium | 780 | 1017 | 509 | 390 |
| Oxygen | 735 | 830 | 415 | 368 |
| Oxygen | 780 | 888 | 444 | 390 |
| Nitrogen | 735 | 887 | 443 | 368 |
| Nitrogen | 780 | 953 | 477 | 390 |

What is claimed is:

1. A method of using laser light for medical therapy comprising the steps of
    selecting a target wavelength within a certain wavelength region for medical application,
    selecting a combination of a laser and a Raman shifter such that said laser can emit a laser beam having a preselected wavelength which, when passed through said Raman shifter, can produce frequency-upshifted light with said target wavelength by anti-Stokes effect,
    applying a photosensitizer to a target region,
    causing said laser to emit a laser beam with said preselected wavelength and to have said laser beam with said preselected wavelength to pass through said Raman shifter to thereby produce Raman-emitted frequency-upshifted light with said target wavelength, and
    causing said Raman-emitted light with said target wavelength to be made incident on said target region for said therapy.

2. The method of claim 1 wherein said laser is a turnable solid state laser.

3. The method of claim 2 wherein said laser is an alexandrite laser.

4. The method of claim 1 wherein said laser is a titanium sapphire laser.

5. The method of claim 1 wherein said target wavelength is between 630 nm and 690 nm.

6. The method of claim 1 wherein said photosensitizer is dihematoporphyrin-ether and said target wavelength is 630 nm.

7. The method of claim 1 wherein said photosensitizer is benzo-porphyrin derivative and said target wavelength is 690 nm.

8. The method of claim 1 wherein said photosensitizer is tin(4)etiopurpurin dichloride and said target wavelength is 660 nm.

9. The method of claim 1 wherein said target wavelength is selected such that laser light of said target wavelength can activate said photosensitizer for photodynamic therapy.

10. The method of claim 1 wherein said laser is a Q-switched laser.

11. The method of claim 1 wherein said laser is a mode-locked laser.

12. The method of claim 1 wherein said Raman-shifter is contained in said laser.

13. The method of claim 1 further comprising the step of introducing a harmonic generator into said combination such that emission at said target wavelength is produced also through passage through said harmonic generator.

14. A method of using laser light for medical therapy comprising the steps of
    selecting a first target wavelength for laser beam to be used for treatment,
    selecting a second target wavelength for laser beam to be used for detection of disorders,
    selecting a combination of a laser and a Raman shifter such that said laser can emit a laser beam having a preselected wavelength which, when passed through said Raman shifter, can produce by anti-Stokes effect frequency-upshifted emission with both said first target wavelength and said second target wavelength,
    causing said laser to emit a laser beam with said preselected wavelength and to have said laser beam with said preselected wavelength to pass through said Raman shifter to thereby produce Raman-emitted frequency-upshifted light with both said first target wavelength and said second target wavelength, and
    selectably (1) applying a photosensitizer to a selected treatment region and causing said Raman-emitted frequency-upshifted light with said first target wavelength to be made incident on said selected treatment region for said treatment or (2) causing said Raman-emitted frequency-upshifted light with said second target wavelength to be made incident on a selected detection region for said detection of disorders.

15. The method of claim 14 wherein said laser is a tunable solid state laser.

16. The method of claim 15 wherein said laser is an alexandrite laser.

17. The method of claim 14 wherein said laser is a titanium sapphire laser.

18. The method of claim 14 wherein said first target wavelength is between 630 nm and 690 nm.

19. The method of claim 14 wherein said photosensitizer is dihematoporphyrin-ether and said first target wavelength is 630 nm.

20. The method of claim 14 wherein said first target wavelength is selected such that laser light of said first target wavelength can activate said photosensitizer for photodynamic therapy.

21. A method of using laser light for medical therapy comprising the steps of
    selecting a first target wavelength for laser beam to be used for treatment,
    selecting a second target wavelength for laser beam to be used for detection of disorders,
    selecting a combination of a laser, a Raman shifter and a harmonic generator such that said laser can emit a laser beam having a preselected wavelength which, when passed through said Raman shifter, can produce by anti-Stokes effect Raman-emitted frequency-upshifted light with said first target wavelength and, when passed through said harmonic generator, can produce laser light with said second target frequency,
    selectably (1) applying a photosensitizer to a selected treatment region and causing said laser to emit a laser beam with said preselected wavelength, causing said emitted laser beam with said preselected wavelength to pass through said Raman shifter to thereby produce Raman-emitted frequency-upshifted light with said first target wavelength and causing said Raman-emitted frequency-upshifted light with said first target wavelength to be made incident on said selected treatment region for said treatment, or (2) causing said laser to emit a laser beam with said preselected wavelength, causing said emitted laser beam with said preselected wavelength to pass through said harmonic generator to thereby produce laser light with said second target frequency and causing said laser light with said second target frequency to be made incident on a selected detection region for said detection of disorders.

22. The method of claim 21 wherein said laser is a tunable solid state laser.

23. The method of claim 22 wherein said laser is an alexandrite laser.

24. The method of claim 21 wherein said laser is a titanium sapphire laser.

25. The method of claim 21 wherein said first target wavelength is between 630 nm and 690 nm.

26. The method of claim 21 wherein said photosensitizer is dihematoporphyrin-ether and said first target wavelength is 630 nm.

27. The method of claim 21 wherein said first target wavelength is selected such that laser light of said first target wavelength can activate said photosensitizer for photodynamic therapy.

* * * * *